(12) United States Patent
Henneken et al.

(10) Patent No.: US 10,555,722 B2
(45) Date of Patent: Feb. 11, 2020

(54) CATHETER TRANSDUCER WITH STAGGERED COLUMNS OF MICROMACHINED ULTRASONIC TRANSDUCERS

(71) Applicant: KONINKLIJKE PHILIPS N.V., Eindhoven (NL)

(72) Inventors: Vincent Adrianus Henneken, Eindhoven (NL); Marcus Cornelis Louwerse, Eindhoven (NL); Ronald Dekker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 283 days.

(21) Appl. No.: 15/533,776

(22) PCT Filed: Dec. 10, 2015

(86) PCT No.: PCT/EP2015/079180
§ 371 (c)(1),
(2) Date: Jun. 7, 2017

(87) PCT Pub. No.: WO2016/091985
PCT Pub. Date: Jun. 16, 2016

(65) Prior Publication Data
US 2017/0319180 A1 Nov. 9, 2017

(30) Foreign Application Priority Data
Dec. 11, 2014 (EP) .................... 14197426

(51) Int. Cl.
*A61B 5/055* (2006.01)
*A61B 8/00* (2006.01)
(Continued)

(52) U.S. Cl.
CPC .............. *A61B 8/4494* (2013.01); *A61B 8/12* (2013.01); *B06B 1/0292* (2013.01)

(58) Field of Classification Search
None
See application file for complete search history.

(56) References Cited

U.S. PATENT DOCUMENTS 5,997,479 A 12/1999 Savord et al.
6,013,032 A 1/2000 Savord
(Continued)

FOREIGN PATENT DOCUMENTS

WO 2010082993 A2 7/2010

OTHER PUBLICATIONS

Zhuang et al "Flexible Transducer Arrays With Through-Wafer Electrical Interconnects Based on Trench Refilling With PDMS" Micro Electro Mechanical Systems, 2007 MES. IEEE 20th International Conference in IEEE. Jan. 1, 2007, p. 73-76.

*Primary Examiner* — Ali Naraghi (57) ABSTRACT

A CMUT transducer array comprising a first column (58) of spaced CMUT cells on at least one silicon island, a second column (58) of spaced CMUT cells on at least one further silicon island, the second column being staggered in alignment with the first column such that cells of the second column are partially located in spaces between successive cells of the first column, the first column and the second column being spaced apart by a gap, and a flexible foil retaining the respective silicon islands, the flexible foil comprising conductive interconnects.

13 Claims, 6 Drawing Sheets

(51) Int. Cl.
*A61B 8/12* (2006.01)
*B06B 1/02* (2006.01)

(56) References Cited

U.S. PATENT DOCUMENTS

| | | |
|---|---|---|
| 6,283,919 B1 | 9/2001 | Roundhill et al. |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 8,332,046 B2 * | 12/2012 | Anderson .......... A61B 5/04001 |
| | | 607/116 |
| 9,539,854 B2 | 1/2017 | Klootwijk et al. |
| 10,092,270 B2 * | 10/2018 | Dirksen .................. A61B 8/00 |
| 2005/0054954 A1 | 3/2005 | Lidgren et al. |
| 2005/0096546 A1 * | 5/2005 | Hazard ................ B06B 1/0292 |
| | | 600/447 |
| 2006/0075818 A1 | 4/2006 | Huang et al. |
| 2009/0058228 A1 | 3/2009 | Wakabayashi et al. |
| 2010/0198070 A1 | 8/2010 | Asafusa et al. |
| 2011/0093052 A1 | 4/2011 | Anderson et al. |
| 2012/0010538 A1 | 1/2012 | Dirksen |
| 2013/0030302 A1 | 1/2013 | Hossack et al. |
| 2013/0116561 A1 | 5/2013 | Rothberg et al. |
| 2013/0155817 A1 | 6/2013 | Kim |
| 2013/0289410 A1 | 10/2013 | Cho et al. |
| 2014/0005521 A1 * | 1/2014 | Kohler ................... A61B 5/064 |
| | | 600/411 |
| 2014/0058294 A1 | 2/2014 | Gross et al. |
| 2015/0087993 A1 * | 3/2015 | Sato ........................ A61B 8/12 |
| | | 600/462 |
| 2016/0199030 A1 * | 7/2016 | Patil ......................... B06B 1/02 |
| | | 600/459 |

* cited by examiner

CATHETER TRANSDUCER WITH STAGGERED COLUMNS OF MICROMACHINED ULTRASONIC TRANSDUCERS

This application is the U.S. National Phase application under 35 U.S.C. § 371 of International Application No. PCT/EP2015/079180, filed on Dec. 10, 2015, which claims the benefit of EP Application Serial No. 14197426.1, filed Dec. 11, 2014. These applications are hereby incorporated by reference herein.

FIELD OF THE INVENTION

This invention relates to medical diagnostic ultrasonic imaging and, in particular, to ultrasonic imaging catheters which use capacitive micromachined ultrasonic transducers (CMUTs).

BACKGROUND OF THE INVENTION

Intra-vascular, e.g. intra-cardiac, ultrasonic imaging catheters are used to examine the vasculature of the body, the heart, and surrounding tissue and organs. When the vasculature and its structures are being examined, the target anatomy is generally very close to the acoustic aperture and only limited acoustic penetration is necessary. These applications call for a high frequency transducer to maximize resolution while relaxing penetration requirements. For an array transducer this means that the array transducer elements should have a small pitch, the center-to-center spacing of adjacent elements, to reduce grating lobes and resultant image clutter. With piezoceramic transducers the pitch is often limited by the dicing process. Micromachined ultrasonic transducer (MUT) arrays, however, can be made very small since they are made by semiconductor processes. Hence, smaller pitch values can generally be obtained when CMUT and other MUT devices are used for the transducer array. The small sizes of MUT devices are advantageous for intra-cardiac catheters, when the array must be fabricated on the tip of a catheter that is sized to be threaded through the cardiovascular system. But other catheter applications call for the imaging of more distant organs and structures. For these applications greater penetration is needed and frequencies can be lower than for near field objects. The greater penetration requires greater transmitted acoustic pressures which is best met by high density arrays. Higher density array elements improve the performance in both the near and far field. It is thus desirable to be able to space adjacent MUT elements very tightly to improve pitch requirements, energy requirements, sensitivity, and hence imaging performance. Intra-cardiac catheters provide a further challenge beyond their small size requirements, which is that the transducer arrays must generally be curved to wrap around the cylindrical tip of the catheter. Such transducer arrays are sometimes referred to as sideways looking arrays.

Figure 7:
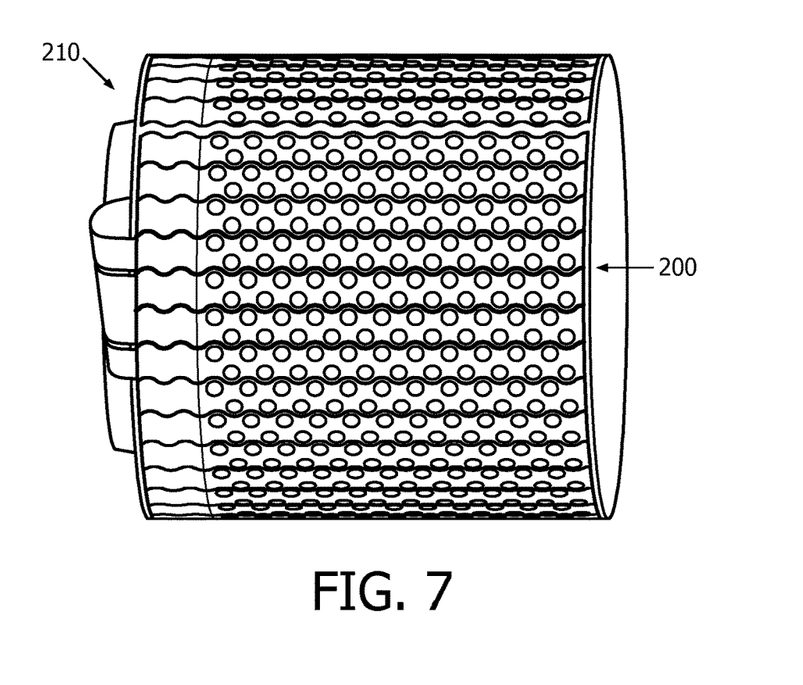
FIG. 7 illustrates the CMUT array of FIG. 6 when wrapped in a cylindrical configuration.

EP 2 455 133 A1 discloses in FIG. 7 a catheter comprising such a sideways looking arrangement of CMUT arrays, wherein each array is separated by a neighboring array by a strip of electrical connections that facilitates the wrapping of the arrangement around the catheter. Although such arrangements can be effectively used in high-intensity focused ultrasound applications in which surrounding tissue may be treated with ultrasound, such arrangements are less suitable for imaging applications in which the discontinuity between neighboring arrays negatively impacts the imaging quality and resolution. Moreover, the CMUT arrays are typically mounted on rectangular rigid silicon islands.

SUMMARY OF THE INVENTION

The present invention seeks to provide a CMUT transducer array that can be wrapped around a catheter and facilitates improved imaging with the array.

The present invention further seeks to provide a catheter comprising such a CMUT transducer array.

The present invention yet further seeks to provide an ultrasound imaging system comprising such a catheter.

According to an aspect, there is provided an CMUT transducer array comprising a first column of spaced CMUT cells on at least one silicon island; a second column of spaced CMUT cells on at least one further silicon island, the second column being staggered in alignment with the first column such that cells of the second column are partially located in spaces between successive cells of the first column, the first column and the second column being spaced apart by a gap; and a flexible foil retaining the respective silicon islands, the flexible foil comprising conductive interconnects.

In accordance with the principles of the present invention, such an ultrasonic transducer CMUT cell array for an intra-cardiac or intravascular catheter is formed in staggered rows of CMUT elements. By staggering the columns the cells of one column can be interspersed among the cells of an adjacent column, providing a smaller array pitch in both the steered direction without necessarily increasing the pitch in the unsteered direction. To be able to bend the array for curved array and catheter applications the elements of the array are fabricated on silicon islands of as few as one or several cells per island, and the island are joined by an integral flexible foil overlay that facilitates a continuous sideways looking array of CMUT cells to be fully wrapped around a 3-dimensional body, e.g. a cylindrical body such as a catheter sheath without discontinuities between array domains. This therefore facilitates the generation of ultrasound images with improved image quality and reduced image artefacts such as grating lobes due to the reduced pitch between CMUT cells.

In a particularly advantageous embodiment, the first column of spaced CMUT cells is located on a first silicon island having opposing meandering edges, each edge meandering outwardly around one of the CMUT cells and meandering inwardly into a space between the CMUT cells; the second column of spaced CMUT cells is located on a second silicon island having opposing meandering edges, each edge meandering outwardly around one of the CMUT cells and meandering inwardly into a space between the CMUT cells; and the first silicon island is arranged adjacent to the second silicon island such that an outwardly meandering edge portion of the first silicon island slots into an inwardly meandering edge portion of the second silicon island.

Such an array benefits from the structural integrity provided by each silicon island carrying a plurality (i.e. a column) of CMUT cells, with the shape of the silicon islands facilitating a particular dense packing of the silicon islands to yield the staggered array of CMUT cells. In addition, due to the fact that the silicon islands may be arranged along the length of a catheter, the resulting transducer array combines good structural integrity with excellent flexibility of the array.

In an embodiment, the first silicon island and the second silicon island each comprise a pair of said columns of spaced CMUT cells, wherein the columns in said pair are staggered.

This limits the number of separate silicon islands in the array whilst still providing excellent flexibility of the array due to the limited width of the respective silicon islands.

The flexible foil may extend over the entire array, thereby keeping the individual silicon islands together whilst providing the array with its desired flexibility. Alternatively, to further increase flexibility of the individual silicon islands relative to each other, the flexible foil may be a patterned foil comprising a plurality of flexible bridges, each flexible bridge extending over a gap between neighboring silicon islands. This for instance facilitates curving the array in multiple directions, e.g. to form a convex or concave transducer array.

Each flexible bridge may comprise a conductive interconnect to electrically interconnect neighboring silicon islands to each other, i.e connect CMUT cells neighboring silicon islands.

Each conductive interconnect may comprise a metal layer embedded in a polymer layer or polymer layer stack to provide electrical insulation to the metal layer.

In at least some embodiments, the metal layer comprises aluminium. This has the advantage that the metal layer may be manufactured without requiring major redevelopment of existing semiconductor manufacturing processes, e.g. CMOS manufacturing processes, as aluminium is routinely used in these processes.

According to another aspect, there is provided a catheter comprising an external sheath and the CMUT transducer array of any of the above embodiments wrapped around the external sheath such that the respective rows of the array extend in a length direction of the catheter. Such a catheter benefits from improved imaging capability due to the continuous nature of the CMUT transducer array wrapped around its external sheath.

The catheter may additionally comprise a further CMUT transducer array at a distal end of the catheter, e.g. at the distal tip of the catheter, to further enhance the imaging capability of the catheter. Such a catheter for instance may be able to generate look ahead images with the further CMUT transducer array as well as 360° images with the CMUT transducer array.

In some embodiments, the catheter may be an intracardiac or an intravascular catheter.

According to another aspect, there is provided an ultrasound imaging system comprising a patient interface module and the catheter according to any of the above embodiments. Such an ultrasound imaging system is capable of generating particularly high quality ultrasound images.

The ultrasound imaging system may further comprise a microbeamformer coupled to the CMUT cells and adapted to steer ultrasonic beams in the row direction; and a DC bias circuit, wherein at least one of the microbeamformer and the DC bias circuit is housed in the patient interface module. The bias circuit may be adapted to operate the CMUT cells in a collapsed mode. By operating the CMUT cells in the collapsed mode, improved output pressure and therefore imaging depth can be generated by the ultrasound transducer array.

DETAILED DESCRIPTION OF THE INVENTION

Figure 1:
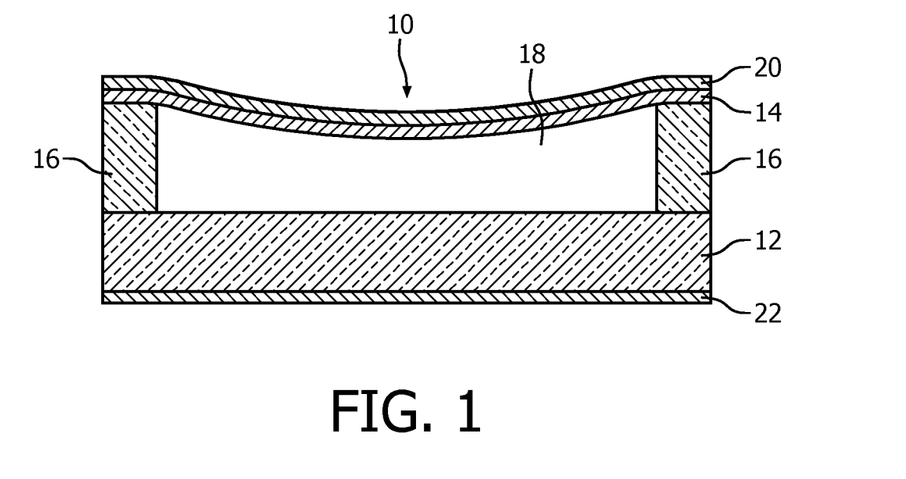
FIG. 1 is a cross-sectional view of a typical suspended membrane CMUT transducer cell.

CMUTs were initially constructed to operate in what is now known as a suspended or "uncollapsed" mode. Referring to FIG. 1, a typical uncollapsed CMUT transducer cell 10 is shown in cross-section. The CMUT transducer cell 10 is fabricated along with a plurality of similar adjacent cells on a substrate 12 such as silicon. A diaphragm or membrane 14 which may be made of silicon nitride is supported above the substrate by an insulating support 16 which may be made of silicon oxide or silicon nitride. The cavity 18 between the membrane and the substrate may be air or gas-filled or wholly or partially evacuated. A conductive film or layer 20 such as gold forms an electrode on the diaphragm, and a similar film or layer 22 forms an electrode on the substrate. These two electrodes, separated by the dielectric cavity 18, form a capacitance. When an acoustic signal causes the membrane 14 to vibrate the variation in the capacitance can be detected, thereby transducing the acoustic wave into a corresponding electrical signal. Conversely, an a.c. signal applied to the electrodes 20,22 will modulate the capacitance, causing the membrane to move and thereby transmit an acoustic signal.

Figure 2:
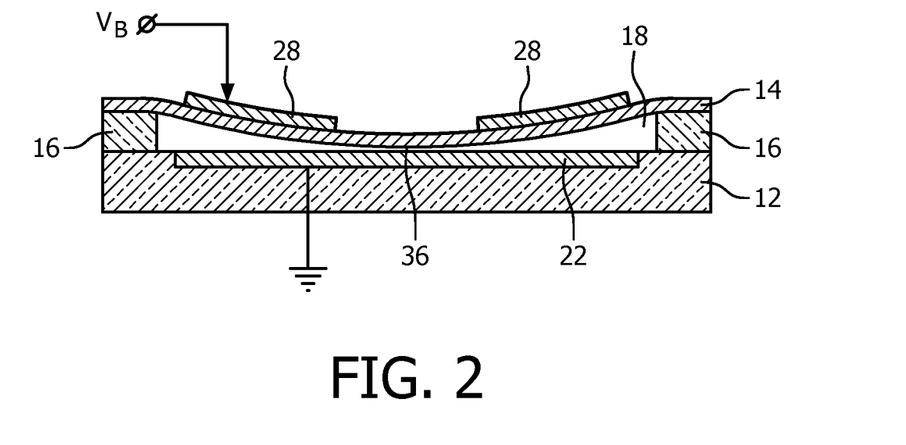
FIG. 2 is a cross-sectional view of a CMUT cell being operated in the collapsed mode.

FIG. 2 is a schematic cross-section of a CMUT cell which is operated in the collapsed mode. The CMUT cell includes a substrate layer 12 such as silicon, a substrate electrode 22, a membrane layer 14, and a membrane electrode ring 28. In this example, the electrode 22 is circularly configured and embedded in the substrate layer 12. In addition, the membrane layer 14 is fixed relative to the top face of the substrate layer 12 and configured/dimensioned so as to define a spherical or cylindrical cavity 18 between the membrane layer 14 and the substrate layer 12. The cell and its cavity 18 may define alternative geometries. For example, cavity 18 could define a rectangular and/or square cross-section, a hexagonal cross-section, an elliptical cross-section, or an irregular cross-section.

The bottom electrode 22 is typically insulated on its cavity-facing surface with an additional layer (not pictured). A preferred insulating layer is an oxide-nitride-oxide (ONO) dielectric layer formed above the substrate electrode and below the membrane electrode. The ONO-dielectric layer advantageously reduced charge accumulation on the electrodes which leads to device instability and drift and reduction in acoustic output pressure. The fabrication of ONO-dielectric layers on a CMUT is discussed in detail in European patent application no. 08305553.3 by Klootwijk et al., filed Sep. 16, 2008 and entitled "Capacitive micromachined ultrasound transducer." Use of the ONO-dielectric layer is desirable with collapsed mode CMUT, which are more susceptible to charge retention than are uncollapsed device. Alternatively, the dielectric layer may comprise a high-k dielectric, such as aluminium oxide or hafnium oxide. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fab, for example, the oxide and nitride layers may be formed by chemical vapor deposition and the metallization (electrode) layer put down by a sputtering process. Suitable CMOS processes are atomic layer deposition (ALD), LPCVD and PECVD, the latter having a relatively low operating temperature of less than 400° C.

Exemplary techniques for producing the disclosed cavity 18 involve defining the cavity in an initial portion of the membrane layer 14 before adding a top face of the membrane layer 14. Other fabrication details may be found in U.S. Pat. No. 6,328,697 (Fraser). In the exemplary embodiment depicted in FIG. 2, the diameter of the cylindrical cavity 18 is larger than the diameter of the circularly configured electrode plate 22. Electrode ring 28 may have the same outer diameter as the circularly configured electrode plate 22, although such conformance is not required. Thus, in an exemplary embodiment of the present invention, the electrode ring 28 is fixed relative to the top face of the membrane layer 14 so as to align with the electrode plate 22 below.

In FIG. 2 the CMUT cell membrane layer is biased to a collapsed state, in which the membrane 14 is in contact with the floor of the cavity 18. This is accomplished by applying a DC bias voltage to the two electrodes as indicated by voltage $V_B$ applied to the electrode ring 28 and a reference potential (ground) applied to the substrate electrode 22. While the electrode ring 28 could also be formed as a continuous disk without the hole in the center, FIG. 2 illustrates why this is not necessary. When the membrane 14 is biased to its precollapsed state as shown in this drawing, the center of the membrane is in contact with the floor of the cavity 18. As such, the center of the membrane 14 does not move during operation of the CMUT. Rather, it is the peripheral area of the membrane 14 which moves, that which is above the remaining open void of the cavity 18 and below the ring electrode. By forming the membrane electrode 28 as a ring, the charge of the upper plate of the capacitance of the device is located above the area of the CMUT which exhibits the motion and capacitive variation when the CMUT is operating as a transducer. Thus, the coupling coefficient of the CMUT transducer is improved.

Figure 3:
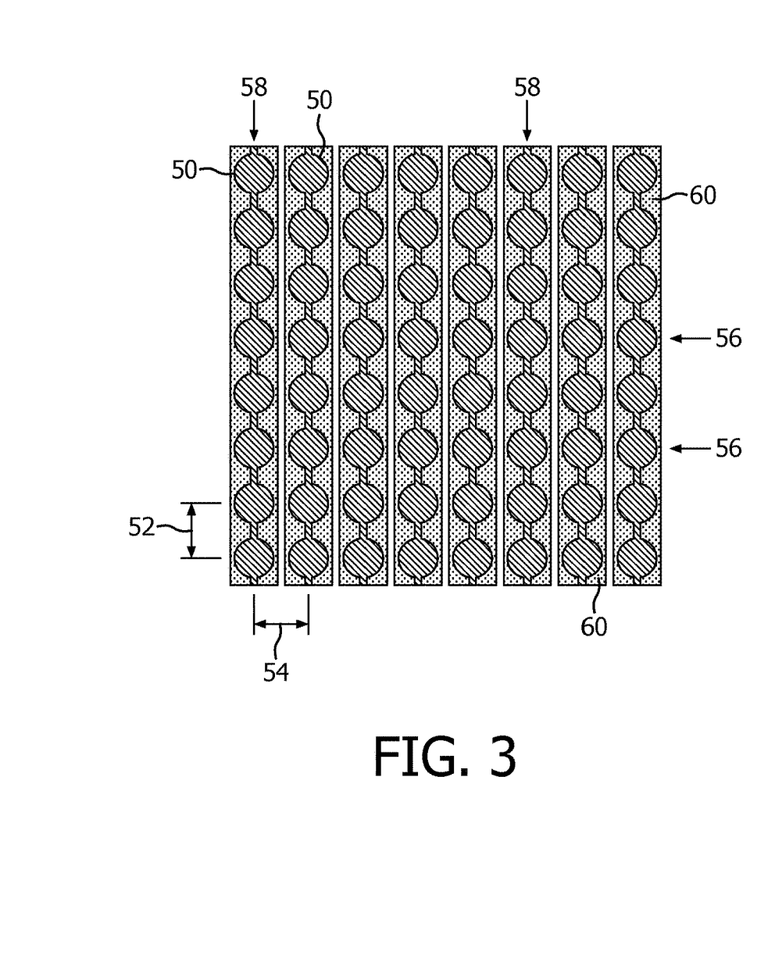
FIG. 3 is a plan view of a symmetrically arranged MUT array of rows and columns of MUT cells.

FIG. 3 is a plan view of a two dimensional array of circular CMUT cells 50. The array is configured in the conventional manner of symmetrically aligned rows 56 and columns 58 of CMUT cells. In this example each column 58 is covered with an integral flexible foil containing embedded metal tracks, which allow the columns to be bent in a cylindrical shape. The flexible foil will be described in greater detail below. In this example the array is dimensioned to have the same pitch in both the row and column directions, as indicated by arrow 52 which denotes the pitch in the column direction and arrow 54 which denotes the pitch in the row direction.

Figure 4:
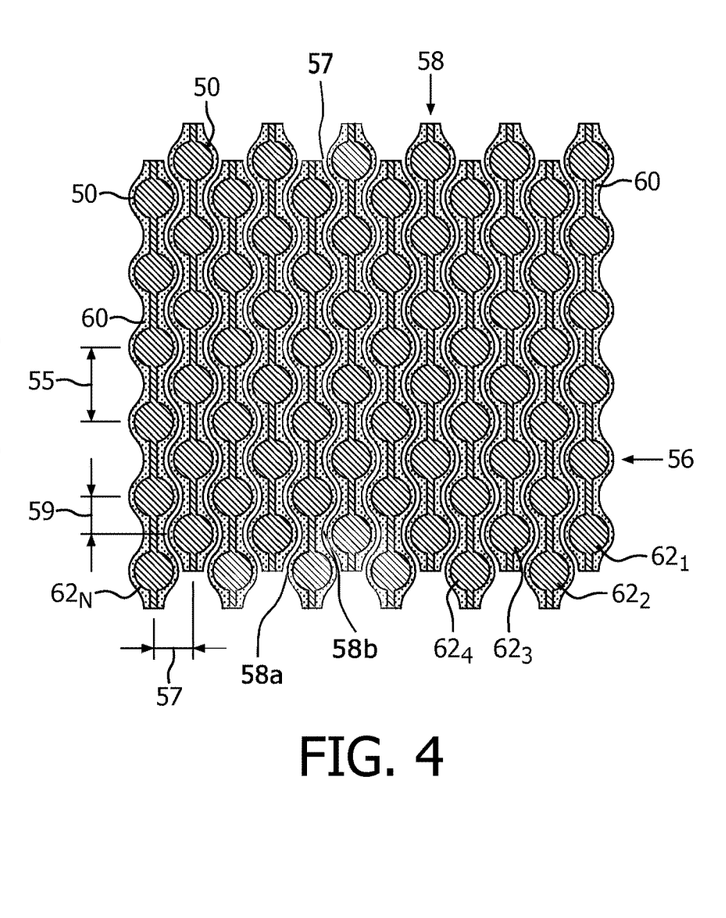
FIG. 4 is a plan view of a MUT array configured with staggered rows of cells with the cells of adjacent rows and columns interspersed within each other.

FIG. 4 is a plan view of a two dimensional array configured in accordance with the principles of the present invention. As shown in FIG. 4, the rows 56 and columns 58 of CMUT cells are staggered in alignment, as is well-known per se. The staggered alignment in this example is accommodated by increasing the spacing 55 between CMUT cells in the columnar direction, which enables adjacent columns and rows to be further interspersed with each other. In an embodiment, the spacing 55 is at least the diameter D of a CMUT cell 50. In the illustrated example the cells are so tightly interspersed that a tangential line from cell to cell in the column or row direction would actually intersect a cell of the adjacent staggered row or column. The interspersion of CMUT cells 50 allows for an increase in the density of CMUT cells within the transducer array without requiring an increase in the vertical spacing (i.e. in the column direction) between CMUT cells 50, at least up to the point where the closest packing of CMUT cells 50 is achieved. Beyond this point, the pitch between successive CMUT elements in the columnar direction may be increased as arrow 55 shows to facilitate a further decrease in horizontal spacing, as indicated by arrows 57 and 59, but this will reduce the overall CMUT density of the transducer array. At least at its closest packing, the CMUT array of FIG. 4 has a greater cell density than the CMUT array of FIG. 3.

In FIG. 4, each column 58 of CMUT cells 50 is located on a separate silicon island, i.e. a separate piece of silicon die. The respective silicon islands are characterized by having a meandering edge structure in the length direction of, i.e. along, the columns 58, with edge portions 58A meandering outwardly around CMUT cells 50 and edge portions 58B meandering inwardly into a space between neighbouring CMUT cells 50 in a column 58. In other words, the columns 58 have wave-shaped opposing edges in the column direction where the wave peaks coincide with the CMUT cells 50 and the wave valleys coincide with the spacings 55 in between the cMUT cells 50.

A neighboring column 58 is arranged such that an outwardly meandering edge portion of its silicon island aligns with, i.e. slots into, an inwardly meandering edge portion of a neighboring silicon island, thereby forming the staggered rows of CMUT cells 50 by the staggered alignment of the CMUT cells 50 between neighbouring columns 58. Neighboring silicon islands are typically separated by a gap 57, to facilitate out-of-plane bending of the silicon islands respective to each other, e.g. when wrapping the CMUT transducer array around a catheter sheath.

In order to retain the relative positions of the silicon islands respective to each other, the CMUT transducer array further comprises a flexible foil 60 onto which the silicon islands are mounted. The flexible foil 60 for instance may comprise a so-called flex-to-rigid foil in which a metal layer or metal layer stack, e.g. metal tracks, is embedded in or covered by a polymer layer or polymer layer stack, which polymer typically is electrically insulating in order to protect the metal layer from accidental short circuits. A non-limiting example of a suitable polymer for such a flexible foil 60 is polyimide, as it is well-known per se that polyimide is compatible with many semiconductor manufacturing processes such as a CMOS manufacturing process. Other suitable polymers, e.g. parylene, will be immediately apparent to the skilled person. A non-limiting example of a suitable metal is aluminium or any other metal commonly used in semiconductor manufacturing processes. The compatibility of such materials with existing semiconductor manufacturing processes facilitates the manufacture of the CMUT transducer array using existing semiconductor manufacturing processes rather than having to redesign or redevelop such manufacturing processes, which would increase the cost of the CMUT transducer array.

The provision of the CMUT cells 50 on a plurality of adjacent meandering silicon islands interconnected via a flexible foil 60 allows for the out-of-plane bending of the CMUT transducer array in the row direction of the array whilst providing structural integrity in the column direction of the array, which for example is particularly advantageous when wrapping the array around a catheter such as an intra-vascular catheter or an intra-cardiac catheter. For example, the CMUT transducer array may be wrapped around the external sheath of such a catheter, with the silicon island columns 58 aligning in a length direction of the catheter, i.e. CMUT transducer array being bent out-of-plane and is wrapped around the catheter sheath in its row direction. Due to the provision of a large number of relatively narrow silicon islands, a near-cylindrical configuration of the CMUT transducer array may be achieved when wrapping the CMUT transducer array around the cylindrical body such as a catheter sheath, with the further advantage that such a CMUT transducer array is continuous over the entire surface of such a body, e.g. does not contain discontinuities between adjacent rectangular silicon islands forming part of the CMUT transducer array, as for instance is the case in EP 2 455 133 A1.

In accordance with a further aspect of the present invention, advantage is taken of this decreased spacing 57 and 59 by operating the array of FIG. 4 so that an operational row of transducer elements is not a horizontal row 56 of elements but an interspersed combination of two (or more) adjacent staggered rows. This is contrary to the conventional wisdom of diced piezoceramic transducer elements, in which an operational row of elements is a perfectly linear row of elements. In the example of FIG. 4, an operational row of elements is formed by staggered rows of elements. For instance, one operational row in FIG. 4 comprises cells $62_1$, $62_2$, $62_3$, $62_4$, . . . $62_N$ of two adjacent staggered rows, i.e. the $M^{th}$ operational row comprises the $M^{th}$ CMUT cell 50 of each column 58 of CMUT cells 50, with M being a positive integer, with each row typically forming a meandering annular row when wrapped around a catheter. The tighter spacing of the staggered rows enables an operational row of 96 cells to be provided where the standard symmetrical alignment would only accommodate 64 cells, for instance, and the staggered configuration of the operational row still is capable of providing acoustic signals for highly resolved images with lower clutter due to the reduced grating lobes in the antenna pattern. Such a staggered row for instance may be addressed by sequentially activating the appropriate CMUT cells 50 of neighboring columns 58, e.g. sequentially activate cells $62_1$, $62_2$, $62_3$, $62_4$, . . . $62_N$ of the N columns 58.

In the embodiment of FIG. 4, the respective silicon islands are retained by a continuous flexible foil 60. In an alternative embodiment, the flexible foil 63 may be patterned such that the flexible foil 60 comprises a plurality of recesses aligning with the gaps 57, with respective bridge portions or bridges extending across the gaps 57 to interconnect different regions of the flexible foil 60, e.g. different regions retaining different silicon islands. This further increases the flexibility of the CMUT transducer but may be less robust.

Figure 5:
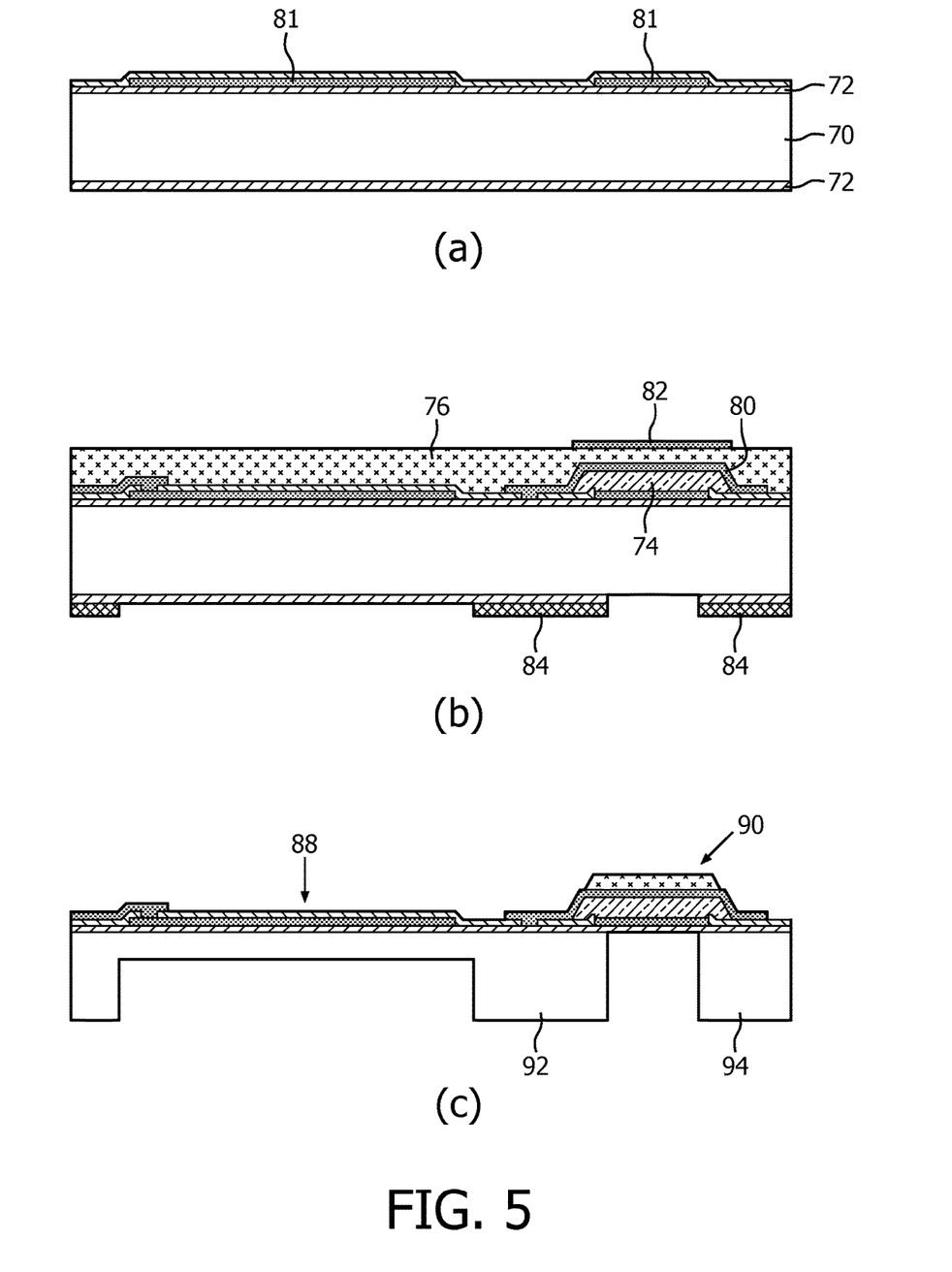
FIG. 5 illustrates steps in the fabrication of a flexible interconnect of adjacent cell silicon islands.

FIG. 5 illustrates several process steps in the formation of a flexible foil bridge joining two silicon islands on which CMUT cells are located. FIG. 5a) shows a silicon wafer 70 with thermal silicon dioxide layers 72 grown on the top and bottom sides. Patterned aluminum areas 81 are sputtered on the top side using standard lithography. A patterned area of polyimide 74 is laid over one of the aluminum areas on the top side, which pattern defines the bridges in the flexible foil. In case of a continuous flexible foil, the polyimide 74 may be a continuous sheet. An aluminum layer 80 is deposited over the polyimide 74 and a second polyimide layer 76 is laid over the aluminum. Another layer of aluminum 82 is patterned over the aluminum layer 80 for use as a mask during etching, all as shown in FIG. 5b). Finally, as shown in FIG. 5c, the silicon wafer 70 is etched away from the back in areas outside the masked by thick resist areas 84, both under CMUT location 88 and under the flexible bridge 74, 80, 76. The polyimide layer 76 on either side of the flexible bridge 90 on the top side is patterned away on either side of etch mask layer 82, which is then itself etched away. The result is two separate silicon islands 92 and 94, joined by a flexible bridge 90. The flexible bridge 90 and others like it enable an array of such CMUT-populated islands to be wrapped in a cylindrical shape, fitting the needs of an intra-cardiac catheter transducer.

Figure 6:
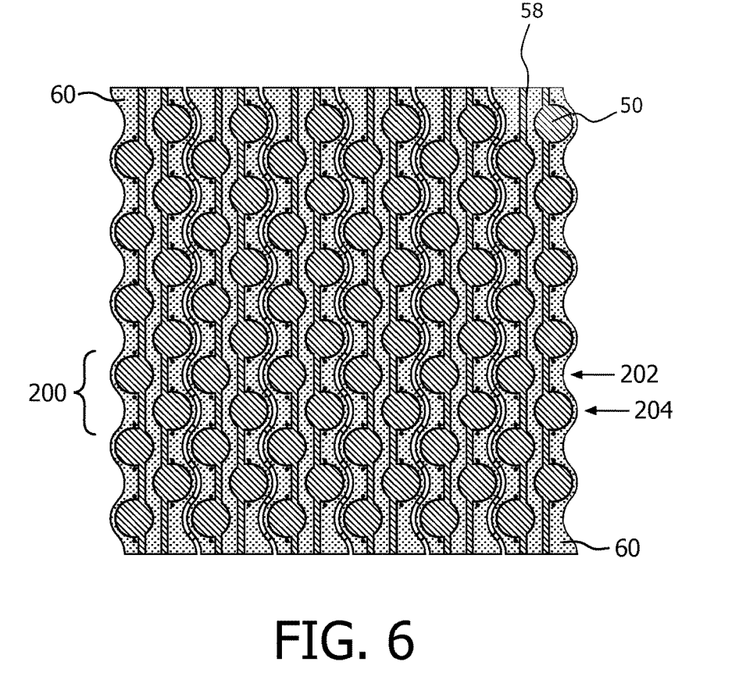
FIG. 6 illustrates the operation of adjacent staggered rows of CMUTs as a single row of transducer elements.

As previously mentioned, an operational row 200 of acoustic transducer elements is formed, not by a straight line of transducer elements as in the conventional manner, but by two or more adjacent staggered rows 202 and 204 of CMUT cells. FIG. 6 schematically depicts an alternative embodiment of an ultrasound transducer array in which each silicon island column 58 comprises a pair of CMUT cell 50 columns arranged in a staggered arrangement, i.e. the area of a CMUT cell 50 in a first column extends into the space between neighboring CMUT cells 50 in the neighboring column, preferably such that a tangent between these neighboring CMUT cells 50 intersects the area of the CMUT cell 50 extending into the space between these neighboring CMUT cells 50.

As before, the silicon island columns 58 have a meandering edge structure in the length direction of, i.e. along, the columns 58, with edge portions meandering outwardly around CMUT cells 50 and edge portions meandering inwardly into a space between neighbouring CMUT cells 50 in a column 58. A neighboring column 58 is arranged such that an outwardly meandering edge portion of its silicon island aligns with, i.e. slots into, an inwardly meandering edge portion of a neighboring silicon island, thereby forming the staggered rows of CMUT cells 50 by the staggered alignment of the CMUT cells 50 between neighbouring columns 58. Neighboring silicon islands are typically separated by a gap 57, to facilitate out-of-plane bending of the silicon islands respective to each other, e.g. when wrapping the CMUT transducer array around a catheter sheath as previously explained.

This embodiment has the advantage of providing larger, i.e. wider, silicon islands, which improves the structural rigidity of such islands, whilst still providing an ultrasound transducer array with excellent flexibility in the row direction. This embodiment is particularly advantageous where the circumference of a body, e.g. a catheter sheath, around which the transducer array is to be wrapped, is many times the width of a single silicon island, such that many silicon islands are to be wrapped around the body, and such that substantially continuous transducer rows are provided around the body.

As before, the direction of operational row 200 is the in-plane, beam-steering direction, i.e. beam steering typically takes place perpendicular to the columns 58. The separate silicon islands are overlaid with a flexible foil 60, e.g. a continuous foil as shown in the drawing or a patterned foil containing bridge portions 90 across the gaps between neighboring silicon islands, to retain the respective orientation of the silicon islands and to enable the two dimensional array to be bent into a cylindrical shape around a distal tip 210 of an intra-cardiac or intravascular catheter as shown in FIG. 7. It should be understood that the array is wrapped around the distal tip 210 by way of non-limiting example only; it is for instance equally feasible to wrap the array around any other part of the catheter, even though it is preferred that the array is located proximal to the distal tip. In some embodiments, the catheter may comprise a further ultrasound transducer array on the distal tip 210, e.g. a planar ultrasound transducer array having a circular circumference in addition to the wraparound ultrasound transducer array according to embodiments of the present invention, such that the catheter can generate images of a body portion ahead of the catheter as well as around the catheter, which for instance is particularly advantageous in intra-cardiac imaging. In some embodiments, the catheter therefore may be an intra-cardiac or intravascular catheter.

Figure 8:
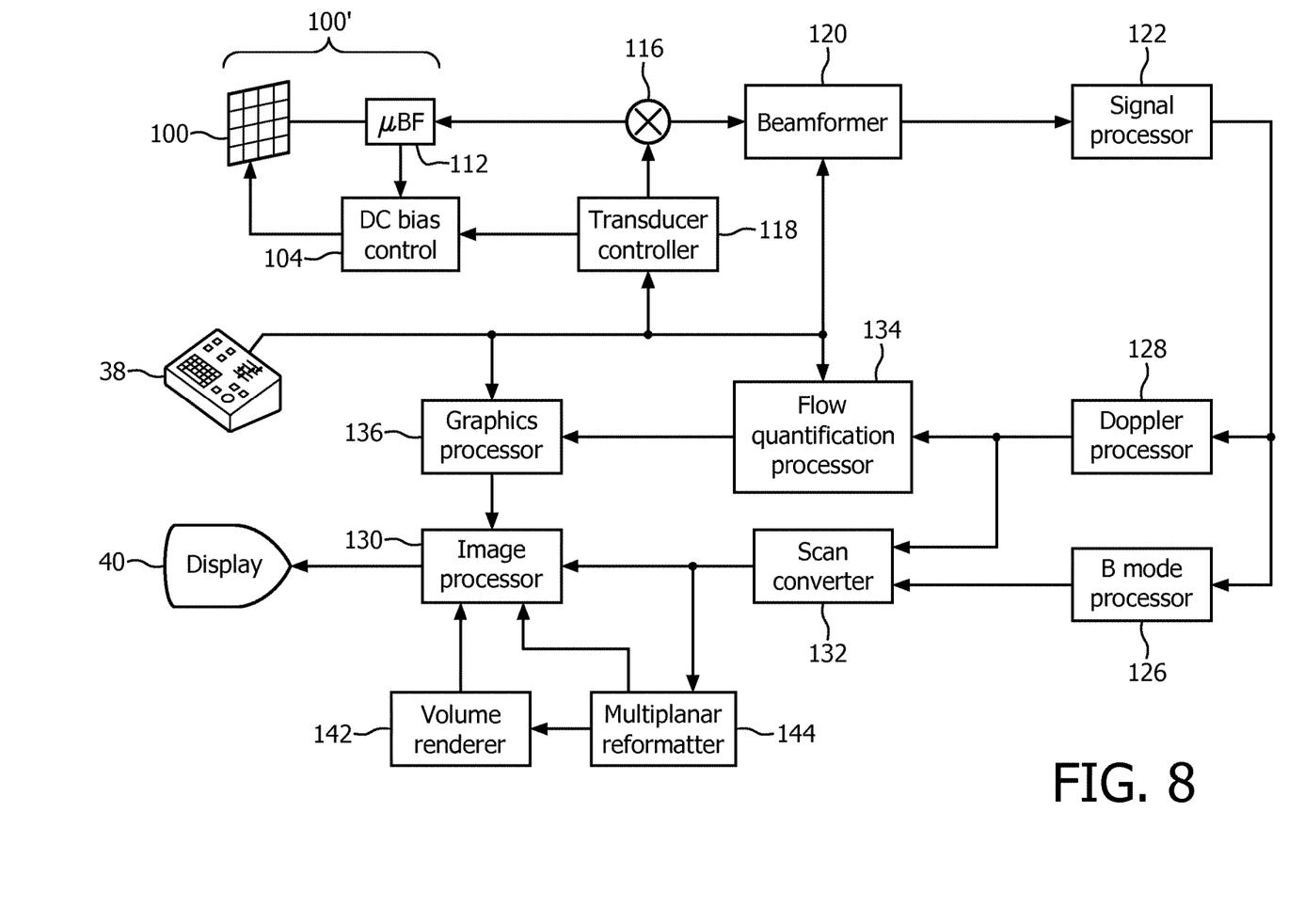
FIG. 8 is a block diagram of an ultrasonic imaging system suitable for use with a staggered CMUT cell array of the present invention.

FIG. 8 illustrates in block diagram form an ultrasound diagnostic imaging system including a staggered row CMUT array on a catheter according to an embodiment of the present invention. The CMUT array 100 may be located on, e.g. wrapped around, the tip (or in the vicinity thereof) of a catheter or ultrasound probe 100', together with a microbeamformer 112. The CMUT array 100 can be a one- or a two-dimensional array of MUT transducer elements capable of scanning in a 2D plane or in three dimensions for 3D imaging. The microbeamformer 112 controls the transmission and reception of signals by the CMUT array cells. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled by the catheter or probe cable to a transmit/receive (T/R) switch 116 which switches between transmission and reception and protects the main system beamformer 120 from high energy transmit signals when a microbeamformer is not used and the transducer array is operated directly by the main system beamformer. The transmission of ultrasonic beams from the CMUT transducer array 100 under control of the microbeamformer 112 is directed by a transducer controller 118 coupled to the T/R switch and the main system beamformer 120, which receives input from the user's operation of the user interface or control panel 38. One of the functions controlled by the transducer controller is the direction in which beams are steered. Beams may be steered straight ahead from (orthogonal to) the transducer array, or at different angles for a wider field of view. The transducer controller 118 also controls the DC bias applied to the CMUT cells which biases the cell membranes 14 to a collapsed state for operation of the CMUTs in the collapsed mode.

The partially beamformed signals produced by the microbeamformer 112 on receive are coupled to a main beamformer 120 where partially beamformed signals from individual patches of transducer elements are combined into a fully beamformed signal. For example, the main beamformer 120 may have 128 channels, each of which receives a partially beamformed signal from a patch of dozens or hundreds of CMUT transducer cells. In this way the signals received by thousands of transducer elements of a CMUT transducer array can contribute efficiently to a single beamformed signal. In a basic implementation the acoustic signals received from two staggered rows of CMUT cells are processed into beams from an image plane in front of the rows of cells to form a scanned 2D image.

The beamformed signals are coupled to a signal processor 122. The signal processor 122 can process the received echo signals in various ways, such as bandpass filtering, decimation, I and Q component separation, and harmonic signal separation which acts to separate linear and nonlinear signals so as to enable the identification of nonlinear echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 126 and a Doppler processor 128. The B mode processor 126 employs amplitude detection for the imaging of structures in the body such as the tissue of organs and vessels in the body. B mode images of structure of the body may be formed in either the harmonic mode or the fundamental mode or a combination of both as described in U.S. Pat. No. 6,283,919 (Roundhill et al.) and U.S. Pat. No. 6,458,083 (Jago et al.) The Doppler processor 128 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 132 and a multiplanar reformatter 144. The scan converter arranges the echo signals in the spatial relationship from which they were received into a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 142 to an image processor 130 for further enhancement, buffering and temporary storage for display on an image display 40. In addition to being used for imaging, the blood flow velocity values produced by the Doppler processor 128 are coupled to a flow quantification processor 134. The flow quantification processor produces measure of different flow conditions such as the volume rate of blood flow. The flow quantification processor may receive input from the user control panel 38, such as the point in the anatomy of an image where a measurement is to be made. Output data from the flow quantification processor is coupled to a graphics processor 136 for the reproduction of measurement values with the image on the display 40. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transmit controller 18 to control the generation of ultrasound signals from the transducer array 100 and hence the images produced by the transducer array and the ultrasound system. The user interface is also coupled to the multiplanar reformatter 144 for selection and control of a display of multiple multiplanar reformatted (MPR) images which may be used to perform quantified measures in the image field of the MPR images. The ultrasound diagnostic imaging system may comprise a patient interface module that may be coupled to the catheter or probe 100', which patient interface module may comprise at least some of the components of the ultrasound diagnostic imaging system. As this is well-known per se, this will not be explained in further detail for the sake of brevity only.

Figure 9:
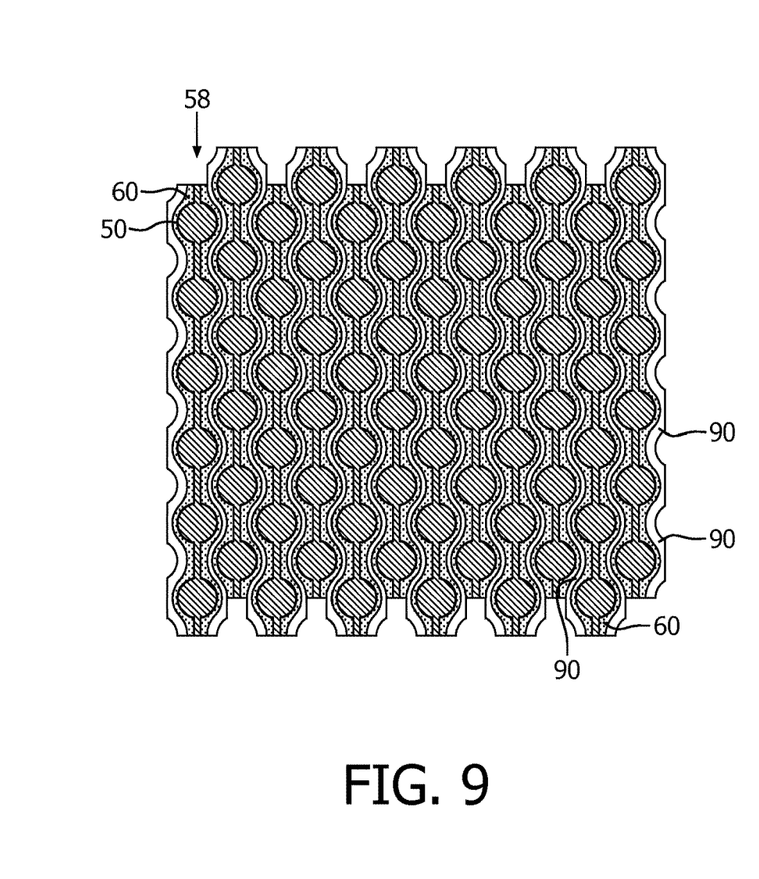
FIG. 9 is a plan view of a MUT array of the present invention with each cell located on its own silicon island and with a flexible foil overlay joined by flexible metallic bridges.
Figure 10:
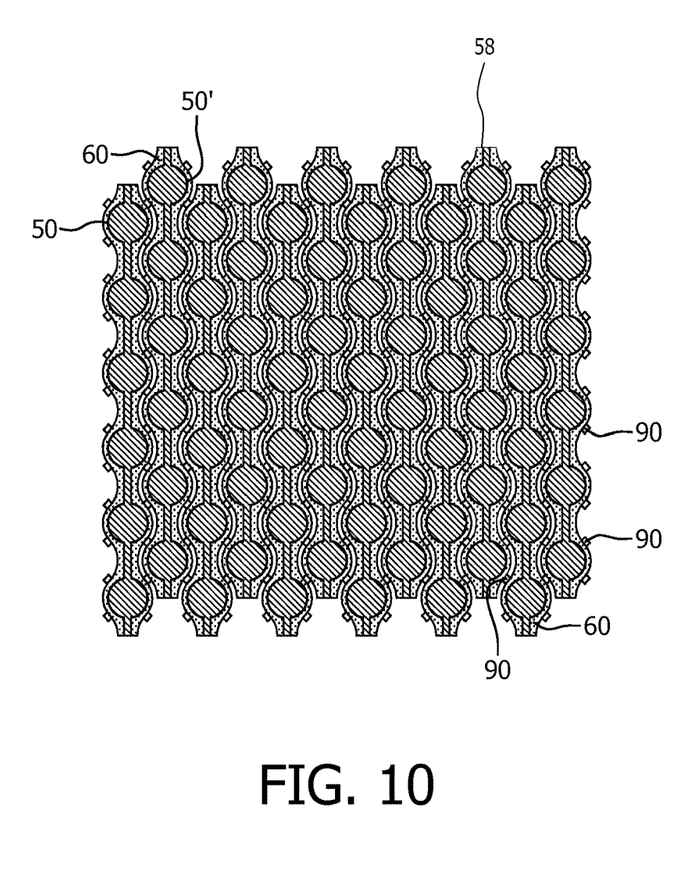
FIG. 10 is a plan view of a MUT array of the present invention with multiple cells located on each silicon island and with a flexible foil overlay joined by flexible metallic bridges.

FIGS. 9 and 10 are plan views of two CMUT arrays according to further embodiments of the present invention. In FIG. 9 each CMUT cell 50 is fabricated on its own silicon island 92 (see FIG. 5). Each column 58 of CMUT cells is overlaid with a strip 60 of flexible foil and the foil strips of adjacent columns are interconnected by flexible bridges 90 which are formed as shown in FIG. 5. The flexible foil strip 60 can comprise a conductive material, such as aluminum, which allows either to address ultrasound elements together within the column, or keeping the elements at the same potential, such as ground. The individual addressing of the elements in the array may be realized via the integrated circuitry. The flexible bridges thus help maintain the orientations of the cells of the array while permitting the array to be flexed and bent in a curved configuration. In particular, in this embodiment the CMUT transducer array may be bent in the row direction as well as in the column direction due to each column 58 being formed by multiple silicon islands interconnected by the bridge structures 90 in the flexible foil strip 60.

FIG. 10 shows a similar CMUT array, except that there are two CMUT cells on each silicon island 92. For instance, CMUT cells 50 and 50' of adjacent columns of elements are both located on the same silicon island. The two adjacent columns are overlaid with a flexible foil strip 60, and adjacent foil strips are interconnected by flexible bridges 90 which permit bending of the array into a curved or cylindrical shape.

As before, it should be understood that instead of a flexible foil strip 60 having discrete portions interconnected by bridge structures 90, a continuous flex foil may be used to retain the respective silicon islands. Such an alternative embodiment is more robust but may have more limited flexibility. This however may not be problematic if the curvature of the body onto which the CMUT transducer array is to be fitted is relatively limited.

The invention claimed is:

1. A CMUT transducer array comprising:
   a first column of spaced CMUT cells on at least one silicon island;
   a second column of spaced CMUT cells on at least one further silicon island, the second column being staggered in alignment with the first column such that cells of the second column are partially located in spaces between successive cells of the first column, the first column and the second column being spaced apart by a gap; and
   a flexible foil retaining the respective silicon islands, the flexible foil comprising conductive interconnects.

2. The CMUT transducer array of claim 1, wherein:
   the first column of spaced CMUT cells is located on a first silicon island having opposing meandering edges, each edge meandering outwardly around one of the CMUT cells and meandering inwardly into a space between the CMUT cells;
   the second column of spaced CMUT cells is located on a second silicon island having opposing meandering edges, each edge meandering outwardly around one of the CMUT cells and meandering inwardly into a space between the CMUT cells; and
   the first silicon island is arranged adjacent to the second silicon island such that an outwardly meandering edge portion of the first silicon island slots into an inwardly meandering edge portion of the second silicon island.

3. The CMUT transducer array of claim 2, wherein the first silicon island and the second silicon island each comprise a pair of said columns of spaced CMUT cells, wherein the columns in said pair are staggered.

4. The CMUT transducer array of claim 1, wherein the flexible foil is a patterned foil comprising a plurality of flexible bridges, each flexible bridge extending over a gap between neighboring silicon islands.

5. The CMUT transducer array of claim 3, wherein each flexible bridge comprises a conductive interconnect.

6. The CMUT transducer array of claim 1, wherein each conductive interconnect comprises a metal layer embedded in a polymer layer or polymer layer stack.

7. The CMUT transducer array of claim 6, wherein the metal layer comprises aluminium.

8. A catheter comprising an external sheath and the CMUT transducer array of claim 1 wrapped around the external sheath such that the respective columns of the array extend in a length direction of the catheter.

9. The catheter of claim 8, further comprising a further CMUT transducer array at a distal end of the catheter.

10. The catheter of claim 8, wherein the catheter is an intra-cardiac or intravascular catheter.

11. An ultrasound imaging system comprising a patient interface module and the catheter of claim 8.

12. The ultrasound imaging system of claim 11, further comprising:

a microbeamformer coupled to the CMUT cells and adapted to steer ultrasonic beams in the row direction; and a DC bias circuit, coupled to the CMUT cells to bias the CMUT cells for operation in the collapsed mode, wherein at least one of the microbeamformer and the DC bias circuit is housed in the patient interface module.

13. The ultrasound imaging system of claim 11, wherein the DC bias circuit is adapted to operate the CMUT cells in a collapsed mode.

* * * * *